US006828443B1

(12) United States Patent
Hollenberg et al.

(10) Patent No.: US 6,828,443 B1
(45) Date of Patent: Dec. 7, 2004

(54) DYES AND COLORANTS

(75) Inventors: Detlef Hollenberg, Erkrath (DE); Horst Hoeffkes, Duesseldorf (DE); Frank Naumann, Duesseldorf (DE); David Rose, Hilden (DE); Leszek J. Wolfram, Stamford, CT (US); Joachim-Kurt Foitzik, Seeheim-Jugenheim (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 15 days.

(21) Appl. No.: 10/031,740

(22) PCT Filed: Jul. 1, 2000

(86) PCT No.: PCT/EP00/06159

§ 371 (c)(1),
(2), (4) Date: Jun. 13, 2002

(87) PCT Pub. No.: WO01/02492

PCT Pub. Date: Jan. 11, 2001

(30) Foreign Application Priority Data

Jul. 6, 1999 (DE) .......................................... 199 30 927

(51) Int. Cl.[7] .............................. C09B 1/28; C09B 1/30; C09B 51/00; C09B 69/00; A61K 7/13
(52) U.S. Cl. ....................... 548/490; 552/228; 552/255; 564/355; 564/370; 564/389; 8/405
(58) Field of Search .......................... 548/490; 552/228, 552/588, 255; 564/355, 370, 389; 8/405

(56) References Cited

U.S. PATENT DOCUMENTS

| | | | | |
|---|---|---|---|---|
| 1,898,693 A | * | 2/1933 | Shepherdson et al. ...... | 552/228 |
| 1,957,599 A | * | 5/1934 | Kalischer et al. ........... | 552/228 |
| 2,311,065 A | * | 2/1943 | McNally et al. ............. | 552/255 |
| 3,817,698 A | | 6/1974 | Kalopissis et al. ........... | 8/10.1 |
| 3,821,200 A | | 6/1974 | Stingl ....................... | 260/239.7 |
| 3,861,868 A | | 1/1975 | Milbrada ..................... | 8/10.2 |
| 3,926,946 A | | 12/1975 | Ridyard ..................... | 260/206 |
| 4,865,774 A | | 9/1989 | Fabry et al. ................ | 252/554 |
| 4,931,218 A | | 6/1990 | Schenker et al. ........... | 252/551 |
| 5,294,726 A | | 3/1994 | Behler et al. ................ | 554/98 |
| 5,534,267 A | | 7/1996 | Neunhoeffer et al. ....... | 424/701 |
| 6,099,592 A | | 8/2000 | Vidal et al. ..................... | 8/409 |
| 6,139,589 A | | 10/2000 | Vidal et al. ..................... | 8/409 |
| 6,165,229 A | | 12/2000 | Vidal et al. ..................... | 8/409 |
| 6,179,882 B1 | | 1/2001 | Vidal et al. ..................... | 8/409 |
| 6,210,447 B1 | | 4/2001 | Vidal et al. ..................... | 8/409 |

FOREIGN PATENT DOCUMENTS

| | | |
|---|---|---|
| CA | 2066226 | 3/1991 |
| DE | 1 083 459 | 6/1960 |
| DE | 19 01 500 | 9/1969 |
| DE | 15 69 819 | 10/1970 |
| DE | 15 69 820 | 11/1970 |
| DE | 22 15 303 | 10/1972 |
| DE | 26 13 425 | 10/1977 |
| DE | 37 23 354 | 1/1989 |
| DE | 37 25 030 | 2/1989 |
| DE | 39 26 344 | 2/1991 |
| DE | 39 29 973 | 3/1991 |
| DE | 40 16 177 | 11/1991 |
| EP | 335477 | * 10/1989 |
| EP | 0 530 229 | 6/1995 |
| EP | 0 740 931 | 11/1996 |
| FR | 2 156 250 | 5/1973 |
| FR | 2 282 456 | 3/1976 |
| FR | 2 456 764 | 12/1980 |
| GB | 1199641 | 7/1970 |
| GR | 1468478 | 3/1977 |
| WO | WO94/08970 | 4/1994 |
| WO | WO97/35550 | 10/1997 |
| WO | WO97/35552 | 10/1997 |
| WO | WO97/35553 | 10/1997 |
| WO | WO98/08485 | 3/1998 |
| WO | WO98/08486 | 3/1998 |
| WO | WO99/20234 | 4/1999 |

OTHER PUBLICATIONS

The Science of Hair Care, Chapter 7, pp. 235–261, published as vol. 7 of Dermatology, Marcel Dekker Inc., NY/Basle (1986).
The Science of hair Care, Chapter 8, pp. 263–286, published as vol. 7 of Dermatology, Marcel Dekker Inc., NY/Basle (1986).
Umbach, Kosmetik, $2^{nd}$ Edition, pp. III–XVIII, George Thieme Verlag, Stuttgart, New York (1995).
Umbach, Kosmetik, $2^{nd}$ Edition, pp. 287–310, George Thieme Verlag, Stuttgart, New York (1995).
K. Schrader, Grundlgen un Rezepturen der Kosmetika [Bases and Formulations in Cosmetics], $2^{nd}$ Edition, pp. 10–23, Huethig Buch Verlag, Heidelberg, Germany (1989).
K. Schrader, Grundlgen un Rezepturen der Kosmetika [Bases and Formulations in Cosmetics], $2^{nd}$ Edition, pp. 782–804, Huethig Buch Verlag, Heidelberg, Germany (1989).

* cited by examiner

*Primary Examiner*—Fiona T. Powers
(74) *Attorney, Agent, or Firm*—Stephen D. Harper; Gregory M. Hill

(57) ABSTRACT

A hybrid dye is provided that is useful for coloring keratin fibers and skin. The hybrid dye has the structure X-S-Y, where X is derived from a substantive dye, Y is derived from an oxidation dye precursor or a melanin precursor, and S is a direct bond or spacer group. The present invention also provides a composition for coloring keratin fibers that contains the hybrid dye.

33 Claims, No Drawings

DYES AND COLORANTS

CROSS REFERENCE TO RELATED APPLICATIONS

This application is a national stage application under 35 U.S.C. § 371 of international application PCT/EP00/06159 filed on Jul. 1, 2000, the international application not being published in English. This application also claims priority under 35 U.S.C. § 119 to DE 199 30 927.2 filed on Jul. 6, 1999.

BACKGROUND OF THE INVENTION

This invention relates to new dyes and dye precursors which are particularly suitable for coloring keratin fibers, to the use of these dyes and dye precursors and to colorants containing these dyes and/or dye precursors.

Among the various products available for the cosmetic treatment of the human body, formulations for modifying or shading the color of the hair occupy a prominent position. Disregarding blonding preparations which lighten the hair oxidatively by degrading the natural hair dyes, three types of colorants have long been of importance in the coloring of hair:

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair.

In recent years, a new coloring process has received considerable attention. In this process, precursors of the natural hair dye, melanin, more particularly derivatives of indole or indoline, are applied to the hair and then form "nature-like" dyes in the hair in the course of oxidative processes. One such process using 5,6-dihydroxyindolines as the dye precursors is described in EP-B1 530 229. If preparations containing 5,6-dihydroxyindoline are applied, in particular repeatedly, people with gray hair can be given back their natural hair color. Color development can be carried out with atmospheric oxygen as sole oxidizing agent so that no other oxidizing agent has to be used.

Although it is possible in principle to formulate colorants containing only a dye or a dye precursor, such colorants are of only limited significance in practice with the exception of a few products which contain melanin precursors for example.

Instead, commercial hair coloring products normally contain a mixture of about 3 to 8 different dyes and/or dye precursors. However, the individual dyes generally differ in their capacity to be absorbed onto the hair and in their fastness to light, perspiration, rubbing and washing which, in addition, can be determined to a considerable extent by the structural properties and condition of the hair. These differences are pronounced above all when substantive dyes are used for adjusting the shade in oxidation hair colorants, as has hitherto been essential for many shades.

Accordingly, there is often a need in the development of new hair colorants to carry out extensive tests not only to obtain certain shades, but above all to ensure that the color is stable for the required period both in regard to shade and in regard to intensity.

It has now surprisingly been found that many of the problems mentioned above can be completely or at least partly avoided by the use of substances which possess both the properties of a substantive dye and the properties of an oxidation dye precursor, a melanin precursor or another substantive dye. In particular, it has been found that the dyes have a very high capacity for absorption onto the hair comparable with that of known hair dyes or hair dye precursors and lead to brilliant intensive hair colors. By virtue of the molecular linkage, the problem of differing fastness properties of the two dyes or dye precursors can thus largely be overcome in many cases.

Substances such as these, which are referred to hereinafter as "hybrid dyes", are new.

SUMMARY OF THE INVENTION

In a first embodiment, there fore, the present invention relates to hybrid dyes, more particularly for coloring keratin fibers, which correspond to formula (I):

where
- X is a group derived from a substantive dye,
- Y is a group derived from
  - an oxidation dye precursor of the secondary or primary intermediate type,
  - a derivative of indole or indoline as a precursor of melanin or
  - a substantive dye and
- S is a direct bond or a spacer group, with the proviso that S is not an alkylene, mono- or polyhydroxyalkylene group where Y is derived from a substantive dye.

DETAILED DESCRIPTION OF THE INVENTION

DE-OSS 15 69 819 and 15 69 820 describe substantive nitro dyes formally composed of two aromatic systems attached by an alkylene or hydroxyalkylene bridge. These dyes have distinctly differing coloring properties from the two starting compounds due largely to the greater molecular weight. However, there is no reference whatever to be found in either of these two documents to the teaching of the present invention.

The compounds corresponding to formula (I) are obtainable by standard synthesis methods of organic chemistry. In this connection, reference is specifically made to the Synthesis Examples in the following.

As mentioned above, the structural principles of known classes of dyes form the basis of the newly developed hybrid dyes.

The group X is derived from compounds which may be assigned to the class of substantive dyes. Preferred classes of substantive dyes from which the group X is derived are:

2-Nitro-1,4-diaminobenzene and its derivatives corresponding to the following general formula:

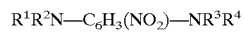

in which the groups $R^1$ to $R^4$ independently of one another stand in particular for hydrogen, a $C_{1-4}$ alkyl group, a $C_{1-4}$ hydroxyalkyl group, a $C_{2-4}$ dihydroxyalkyl group, a $C_{1-4}$ aminoalkyl group, an optionally substituted phenyl group or a $C_{3-8}$ cycloalkyl group.

Particularly preferred representatives of this class of dyes are the compounds known by the INCI names of HC Red No. 3, HC Blue No. 2, HC Blue No. 12 and HC Violet No. 1 and also 1,4-bis-(2'-hydroxyethyl)amino-2-nitrobenzene and 4-amino-2-nitrodiphenyl-amine-2'-carboxylic acid and 2-nitro-1,4-diaminobenzene.

Derivatives of 4-nitro-2-aminophenol

Particularly preferred representatives are picramic acid and salts thereof, more particularly the sodium salt, 2-amino-6-chloro4-nitrophenol and 2-chloro-6-ethylamino4-nitrophenol.

Derivatives of 2-amino-5-nitrophenol

A particularly preferred representative is the compound known by the INCI name of HC Violet No. 4.

Derivatives of 2-nitro-4-aminophenol

Particularly preferred representatives are the compounds known under the INCI name of HC Red BN and 4-(2'-hydroxyethyl)amino-2-nitrophenol.

Derivatives of 2-nitroaniline

Particularly preferred representatives are the compounds known by the INCI names of HC Yellow No. 2 and HC Yellow No. 6 and 4-ethylamino-3-nitrobenzoic acid and N-hydroxyethyl-2-nitro-4-methyl aniline and also 2,4-dinitroaniline.

Derivatives of quinoxaline

A particularly preferred representative is 6-nitro-1,2,3,4-tetrahydro-quinoxaline.

Derivatives of anthraquinone

Particularly preferred representatives are the compounds known by the INCI names of Disperse Blue 3, Disperse Violet 1 and Disperse Violet 4 (CI 61105) and also 1-aminoanthraquinone and 1,4-diaminoanthraquinone-3-sulfonic acid.

Derivatives of naphthoquinone

A particularly preferred representative is the compound known by the INCI name of Basic Blue 99

Azo dyes

Particularly preferred representatives are the compounds known by the INCI names of Basic Yellow 57 (CI 12719), Disperse Orange 3 (CI 11005), Basic Red 76 (CI 12245), Disperse Black 9, Basic Brown 16 (CI 12250) and Basic Brown 17 (CI 12251).

With regard to other substantive dyes from which the group X may be derived, reference is also specifically made to the known reference books, for example Ch. Zviak, The Science of Hair Care, Chapter 7 (pages 248–250), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie-und Handelsunternehmen für Arzneimittel, Reformwaren und Körperpflegemittel e.V., Mannheim, Germany.

The groups X may of course also be derived from naturally occurring substantive dyes such as, for example, henna red, henna neutral, camomile blossom, sandalwood, black tea, black alder bark, sage, logwood, madder root, catechu, sedre and alkanet.

The group Y is a group derived from an oxidation dye precursor of the secondary or primary intermediate type, a derivative of indole or indoline as a precursor of melanin or a substantive dye.

In a first preferred embodiment of the present invention, the group Y is derived from an oxidation dye precursor of the secondary intermediate type.

Preferred classes of oxidation dye precursors of the secondary intermediate type from which the group Y may be derived are:

3-Aminophenol and derivatives thereof

Preferred representatives are 5-amino-2-methylphenol, 5-(3-hydroxypropylamino)-2-methylphenol, 3-amino-2-chloro-6-methyl-phenol, 2-hydroxy4-aminophenoxyethanol, 3-amino-6-methoxy-2-methylaminophenol, 2,6-dimethyl-3-aminophenol, 3-trifluoroacetyl-amino-2-chloro-6-methylphenol, 5-amino-4-chloro-2-methylphenol, 5-amino-4-methoxy-2-methyl-phenol, 5-(2'-hydroxyethyl)-amino-2-methylphenol, 3-dimethylaminophenol, 3-diethylaminophenol, N-cyclopentyl-3-aminophenol, 1,3-dihydroxy-5-(methylamino)-benzene, 3-ethylamino-4-methylphenol and 2,4-dichloro-3-aminophenol.

2-Aminophenol and derivatives thereof, 1,3-Diaminobenzene and derivatives thereof Preferred representatives are 2,4-diaminophenoxyethanol, 1,3-bis-(2,4-diaminophenoxy)-propane, 1-methoxy-2-amino-4-(2'-hydroxy-ethylamino)-benzene, 1,3-bis-(2,4-diaminophenylypropane, 2,6-bis-(2-hydroxyethylamino)-1-methylbenzene, 1-amino-3-bis-(2'hydroxy-ethyl)-aminobenzene, 1,2-bis-(2,4-diaminophenoxy)-benzene and 1,3-bis-(2,4-diaminophenoxyybenzene.

1,2-Diaminobenzene and derivatives thereof

Preferred representatives are 3,4-diaminobenzoic acid and 2,3-diamino-1-methylbenzene.

Di- and trihydroxybenzenes and derivatives thereof

Preferred representatives are resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene and also resorcinol dimethyl ether, Pyridine derivatives Preferred representatives are 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethyl-pyridine, 2,6-dihydroxy-3,4-diaminopyridine, 2,6-dihydroxy-4-methylpyridine, 2,6-diaminopyridine, 2,3-diamino-6-methoxy-pyridine and 3,5-diamino-2,6-dimethoxypyridine.

Naphthalene derivatives

Preferred representatives are 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene and also 1-aminonaphthalene.

Morpholine derivatives

Preferred representatives are 6-hydroxybenzomorpholine and 6-aminobenzomorpholine.

Quinoxaline derivatives

A preferred representative is 6-methyl-1,2,3,4-tetrahydroquinoxaline.

Pyrazole derivatives

A preferred representative is 1-phenyl-3-methylpyrazol-5-one.

Indole derivatives

Preferred representatives are 4-hydroxyindole, 6-hydroxyindole and 7-hydroxyindole.

Methylenedioxybenzene derivatives

Preferred representatives are 3,4-methylenedioxyphenol, 1-amino-3,4-methylenedioxybenzene and 1-(2'-hydroxyethyl)-amino-3,4-methylenedioxybenzene.

Heterocyclic compounds as disclosed in WO 97/35550, WO 97/35552, WO 97/35553, WO 98/08485 and WO 98/08486, to which reference is expressly made.

With regard to other oxidation dye precursors of the secondary intermediate type from which the group Y may be derived, reference is also specifically made to the known reference books, for example Ch. Zviak, The Science of Hair Care, Chapter 8 (pages 264–267), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel e.V., Mannheim, Germany.

In a second preferred embodiment of the present invention, the group Y is derived from an oxidation dye precursor of the primary intermediate type.

Preferred classes of oxidation dye precursors of the primary intermediate type from which the group Y can be derived are:

1,4-Diaminobenzene and derivatives thereof

Preferred representatives are p-phenylenediamine, p-toluylenediamine, 1-(2'-hydroxyethyl)-2,5-diaminobenzene, N,N-bis(2-hydroxyethyl)-p-phenylenediamine, 2-(2,5-diaminophenoxy)-ethanol, 1,3-bis-(N-(2-hydroxyethyl)-N-(4-aminophenyl-amino))-2-propanol, 1,10-bis-(2,5-diaminophenyl1,4,7,10-tetraoxadecane and 1,4-bis-(4-aminophenyl)-diazacycloheptane and corresponding compounds with one or more halogen atoms, more particularly chlorine and fluorine, on the benzene ring.

1,2-Diaminobenzene and derivatives thereof

4-Aminopenol and derivatives thereof

Preferred representatives are p-aminophenol, 2-chloro-4-aminophenol, 4-amino-3-methylphenol, 2-hydroxyethylamino-4-aminophenol, 4,4'-diaminodiphenylamine, 4-amino-3-fluorophenol, 2-aminomethyl-4-aminophenol, 2-hydroxymethyl-4-aminophenol, 4-amino-2-((diethylamino)-methyl)-phenol, bis-(2-hydroxy-5-aminophenyl)-methane, 4-amino-2-(2-hydroxyethoxy)-phenol.

2-Aminophenol and derivatives thereof

A preferred representative is o-aminophenol.

Diaminopyridine derivatives

Heterocyclic hydrazones

4-Aminopyrazole derivatives

Preferred representatives are 1-phenyl-3-carboxyamido-4-amino-5-pyrazolone and 4,5-diaminopyrazole derivatives according to EP 0 740 931 or WO 94/08970 such as, for example, 4,5-diamino-1-(2'-hydroxyethyl)-pyrazole.

Pyrimidine derivatives

Preferred representatives are 2,4,5,6-tetraamino-pyrimidine, 2-hydroxy-4,5,6-triaminopyrimidine, 4-hydroxy-2,5,6-triamino-pyrimidine, 2,4-dihydroxy-5,6-diaminopyrimidine and 2-dimethyl-amino-4,5,6-triaminopyrimidine.

With regard to other oxidation dye precursors of the primary intermediate type from which the group Y may be derived, reference is also specifically made to the known reference books, for example Ch. Zviak, The Science of Hair Care, Chapter 8 (pages 264–267), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel e.V., Mannheim, Germany.

In a third preferred embodiment of the present invention, the group Y is derived from a precursor of melanin selected from the derivatives of indole and indoline. In the context of the present invention, "precursors of melanin" are understood to be derivatives of indole and indoline which are capable of forming melanin dyes or corresponding melanin dye derivatives in an oxidative process.

According to the invention, the groups Y in this embodiment are derived from indoles and indolines which contain at least one hydroxy or amino group, preferably as a substituent on the six-membered ring. These groups may carry other substituents, for example in the form of etherification or esterification of the hydroxy group or alkylation of the amino group. Indoles and indolines containing two of these groups, particularly two hydroxy groups, of which one or both may be etherified or esterified are particularly preferred.

According to the invention, particularly preferred groups Y are derived from derivatives of indoline, such as 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 5-hydroxyindoline, 6-hydroxyindoline, 5-aminoindoline, 6-aminoindoline and 4-aminoindoline.

Most particularly preferred groups Y are derivatives of 5,6-dihydroxyindoline corresponding to formula (IIa):

(IIa)

[Structure: 5,6-dihydroxyindoline derivative with $R^4$—O— and $R^5$—O— substituents on the benzene ring, $R^3$ and $R^2$ on the 5-membered ring, and $R^1$ on the nitrogen]

in which—independently of one another—

$R^1$ is hydrogen, a $C_{1-4}$ alkyl group, a $C_{1-4}$ hydroxyalkyl group or a $C_{3-6}$ cycloalkyl group, $R^2$ is hydrogen or a —COOH group which may even be present as a salt with a physiologically compatible anion, $R^3$ is hydrogen or a $C_{1-4}$ alkyl group, R⁴ is hydrogen, a $C_{1-4}$ alkyl group or a group —CO—R⁶ where R⁶ is a $C_{1-4}$ alkyl group or an optionally substituted phenyl group and R⁵ stands for one of the groups mentioned for R⁴.

According to the invention, preferred representatives are 5,6-dihydroxyindoline, N-methyl-5,6-dihydroxyindoline, N-ethyl-5,6-dihydroxy-indoline, N-propyl-5,6-dihydroxyindoline, N-butyl-5,6-dihydroxyindoline. The parent compound, 5,6-dihydroxyindoline, is most particularly preferred.

According to the invention, preferred indoles from which the group Y is derived are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole, 5,6-dihydroxyindole-2-carboxylic acid, 5-hydroxyindole, 6-hydroxyindole, 5-aminoindole, 6-aminoindole and 4-aminoindole.

Particular preference is attributed to derivatives of 5,6-dihydroxyindole corresponding to formula (IIb):

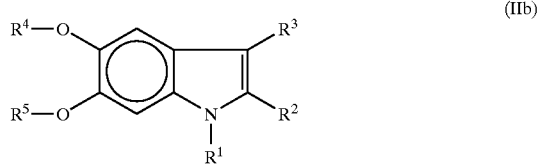

in which—independently of one another—
R¹ is hydrogen, a $C_{1-4}$ alkyl group, a $C_{1-4}$ hydroxyalkyl group or a $C_{3-6}$ cycloalkyl group, R² is hydrogen or a —COOH group which may even be present as a salt with a physiologically compatible anion, R³ is hydrogen, a $C_{1-4}$ alkyl group or a group —CH₂—NR⁷R⁸, where R⁷ and R⁸ independently of one another are hydrogen or a $C_{1-4}$ alkyl group, R⁴ is hydrogen, a $C_{1-4}$ alkyl group or a group —CO—R⁶ where R⁶ is a $C_{1-4}$ alkyl group or an optionally substituted phenyl group and R⁵ stands for one of the groups mentioned for R⁴.

According to the invention, preferred representatives are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole. The parent compound, 5,6-dihydroxyindole, is most particularly preferred.

In a fourth embodiment of the present invention, the group Y derives from a substantive dye. Suitable and preferred dyes Y are derived in principle from the same compounds that are described in detail above in the definition of the group X.

Although, according to the invention, compounds where the groups X and Y are identical are not intended to be excluded from the defined group of hybrid dyes, the compounds according to this embodiment normally contain different groups X and Y. More particularly, the groups X and Y differ in their light absorption capacity to the extent that the wavelengths of the absorption maxima of the two groups differ by at least 30 nm, preferably by at least 50 nm and more particularly by at least 80 nm.

In a first embodiment of the invention, the group S in structural formula (I) stands for a direct bond.

In such cases, the π-electron systems of the groups X and Y will generally interact so that the light absorption behavior of the hybrid dye generally differs distinctly from that of the groups X and Y. As a result, a significantly different color tone is obtained on the hair by comparison with colors formed with a mixture of corresponding dyes which correspond to the groups X and Y.

However, a core object of the present invention is to avoid the problems arising in many areas where complex dye mixtures are used, for example in regard to absorptivity and fastness to washing, without altering either the color tone or the shade.

According to the invention, therefore, it is generally preferred for S to be a spacer group through which no interaction between the π-electron systems of the groups X and Y occurs. Accordingly, S preferably contains at least one carbon atom with sp³ hybridization on the direct connecting line between the groups X and Y.

Preferred spacer groups are:

Alkylene groups corresponding to the general formula —$C_nH_{2n}$—, more particularly —$(CH_2)_n$—, in which n is an integer, preferably a number of 1 to 8 and more particularly a number of 1 to 4.

According to the invention, preferred alkylene groups are the methylene, 1,2-ethylene and 1,3-propylene group.

Cycloaliphatic groups, such as cyclopentyl, cyclohexyl and cycloheptyl groups.

Mono- and polyhydroxyalkylene groups corresponding to the general formula —$C_nH_{2n-x}(OH)_x$—, in which n is an integer, preferably a number of 1 to 8 and more particularly a number of 1 to 4 and x is an integer, more particularly a number of 1 to 3.

Preferred hydroxyalkylene groups are the hydroxymethylene, hydroxy-1,2-ethylene, 2-hydroxy-1,3-propylene, 2,3-dihydroxy-1,3-propylene and 2,3- or 1,4-dihydroxybutylene group.

Dialkyleneamino groups optionally substituted at the alkyl chains, more particularly those corresponding to the general formula —$(CH_2)_n$—N(Z)—$(CH_2)_m$—, in which n and m independently of one another represent an integer of 1 to 8, more particularly 1 to 4, but are preferably the same number, and Z represents hydrogen, a $C_{1-8}$ and more particularly $C_{1-4}$ alkyl group, a $C_{1-8}$ and more particularly $C_{1-4}$ monohydroxyalkyl group, a $C_{2-8}$ and more particularly $C_{2-4}$ dihydroxyalkyl group or a $C_{3-8}$ and more particularly $C_{3-4}$ trihydroxyalkyl group, and those corresponding to the following general formula.

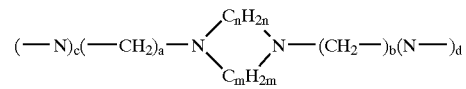

in which a and b independently of one another represent integers of 0 to 4 and c and d stand for 0 or 1, with the proviso that c=0 when a=0 and d=0 when b=0, n is an integer of 1 to 5 and m is an integer of 1 to 3, with the proviso that the sum n+m=3 to 8. The 1,4-piperazino group is particularly preferred.

Trialkylenediamino groups optionally substituted at the alkyl chains, more particularly those corresponding to the general formula: —$(CH_2)_n$—N(Z)—$(CH_2)_m$—N(A)—$(CH_2)_p$—, in which n, m and p independently of one another may represent an integer of 1 to 8 and more particularly 1 to 4, although n and m preferably stand for the same number, and Z and A independently of one another represent hydrogen, a $C_{1-8}$ and more particularly $C_{1-4}$ alkyl group, a $C_{1-8}$ and more particularly $C_{1-4}$ monohydroxyalkyl group, a $C_{2-8}$ and more particularly $C_{2-4}$ dihydroxyalkyl group or a $C_{3-8}$ and more particularly $C_{3-4}$ trihydroxyalkyl group.

Ether groups optionally substituted at the alkyl chains, more particularly those corresponding to the general formula —$(CH_2)_n$—O—$(CH_2)_m$—, in which n and m independently of one another may represent an integer of 1 to 8 and more particularly 1 to 4, but preferably stand for the same number, Polyether groups optionally substituted at the alkyl chains, more particularly those corresponding to the general formula —$(CH_2)_n$—O—$(CH_2)_m$—O—$(CH_2)_m$—$(CH_2)_n$—, in which n and m independently of one another may represent an integer of 1 to 8 and more particularly 1 to 4, but preferably stand for the same number, Sulfur-containing groups, more particularly groups corresponding to the general formula —$(CH_2)_n$—$S(O)_o$—$(CH_2)_m$—in which n and m independently of one another may represent an integer of 1 to 8 and more particularly 1 to 4, but preferably stand for the same number, and o is the number 0, 1 or 2.

The spacers S in the hybrid dyes according to the invention are attached by their two free bonds to the groups X and Y so that they each replace a hydrogen atom as substituent in the dye or dye precursor molecules on which the groups X and Y are based.

In a first preferred embodiment, the spacer group replaces a hydrogen atom directly attached to a ring system of the group X or Y as substituent. Examples of such ring systems are aromatic and cycloaliphatic hydrocarbon ring systems, more particularly benzene, naphthalene, anthracene, naphthoquinone and anthraquinone systems heterocyclic ring systems, more particularly pyridine, pyrazole, pyrimidine, indole and indoline systems.

In a second preferred embodiment, the spacer group S replaces a hydrogen atom of a primary or secondary amino group attached to an aromatic, cycloaliphatic or heterocyclic ring system either directly or through an aliphatic hydrocarbon group as substituent.

In a third embodiment, the spacer group S replaces the hydrogen atom of a hydroxy group attached to an aromatic, cycloaliphatic or heterocyclic ring system either directly or through an aliphatic hydrocarbon group as substituent.

The hybrid dyes according to the invention are eminently suitable for coloring keratin fibers. Keratin fibers in the context of the invention are pelts, wool, feathers and in particular human hair. However, there is nothing to prevent them being used in other fields, particularly color photography.

Accordingly, in a second embodiment, the present invention relates to compositions for coloring keratin fibers, more particularly human hair, which contain a hybrid dye corresponding to structural formula (I). The teaching according to the invention does of course also encompass compositions containing combinations of more than one hybrid dye corresponding to formula (I).

The compositions according to the invention for coloring human hair may also contain any of the ingredients typical of such compositions.

The colorants according to the invention preferably contain at least one other dye, one other dye precursor and/or an indole or indoline derivative as melanin precursor.

In a first embodiment, colorants which contain at least one oxidation dye precursor besides a hybrid dye of formula (I) are particularly preferred. These oxidation dye precursors may be both of the secondary intermediate type and of the primary intermediate type.

Suitable oxidation dye precursors of the primary intermediate type are, for example, primary aromatic amines with another free or substituted hydroxy or amino group in the para or ortho position, diaminopyridine derivatives, heterocyclic hydrazones, 4-aminopyrazole derivatives and 2,4,5,6-tetraaminopyimidine and derivatives thereof.

According to the invention, preferred primary intermediates are p-phenylenediamine, p-toluylenediamine, p-aminophenol, 2-chloro-4-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxyethylaminomethyl-4-aminophenol, 4,4'-diaminodiphenylamine, 4-amino-3-fluorophenol, 2-aminomethyl-4-aminophenol, 2-hydroxymethyl-4-aminophenol, 4-amino-2-((diethylamino)-methyl)-phenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol, 1,10-bis-(2,5-diaminophenyl)-1,4,7,10-tetraoxa-decane and 4,5-diaminopyrazole derivatives according to EP 0 740 931 and WO 94/08970 such as, for example, 4,5-diamino-1-(2'-hydroxyethyl)-pyrazole. Particularly preferred primary intermediates are p-phenylenediamine, p-toluylenediamine, p-aminophenol, 1-(2'-hydroxyethyl2,5-diaminobenzene, 4-amino-3-methylphenol, 2-aminomethyl-4-aminophenol, 2,4,5,6-tetraaminopyrimidine, 2-hydroxy-4,5,6-triaminopyrimidine and 4-hydroxy-2,5,6-triaminopyrimidine.

Suitable oxidation dye precursors of the secondary intermediate type are, for example, m-phenylenediamine derivatives, naphthols, resorcinol and resorcinol derivatives, pyrazolones and m-aminophenol derivatives.

According to the invention, preferred secondary intermediates are m-aminophenol and derivatives thereof such as, for example, 5-amino-2-methylphenol, 5-(3-hydroxypropylamino)-2-methylphenol, 3-amino-2-chloro-6-methylphenol, 2-hydroxy-4-aminophenoxy ethanol, 2,6-dimethyl-3-aminophenol, 3-trifluoroacetylamino-2-chloro-6-methylphenol, 5-amino-4-chloro-2-methylphenol, 5-amino-4-methoxy-2-methyl-phenol, 5-(2'-hydroxyethyl)-amino-2-methyl-phenol, 3-(diethylamino)-phenol, 3-(dimethylamino)-phenol, N-cyclo-pentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, such as 4-chloro-o-aminophenol, m-diaminobenzene and derivatives thereof such as, for example, 2,4-diaminophenoxyethanol, 1,3-bis-(2,4-diaminophenoxy)-propane, 1-methoxy-2-amino4-(2'-hydroxyethylamino)-benzene, 1,3-bis-(2,4-diaminophenyl)-propane, 2,6-bis-(2-hydroxyethylamino)-1-methyl-benzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-3,4-diaminopyridine, 2,6-dihydroxy-4-methylpyridine, 2,6-diaminopyridine, 2,3-diamino-6-methoxy-pyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihdroxynaphthalene, 1,8-dihydroxynaphthalene, 2,7-dihdroxynaphthalene and 2,3-dihydroxynaphthalene, morpholine derivatives such as, for example, 6-hydroxybenzo-morpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, methylenedioxybenzene derivatives such as, for example, 3,4-methylenedioxyphenol, 1-hydroxy-3,4-methylenedioxybenzene, 1-amino-3,4-methylenedioxybenzene and 1-(2'-hydroxyethyl)-amino-3,4-methylenedioxybenzene.

According to the invention, particularly preferred secondary intermediates are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol, 2,6-dihydroxy-3,4-diaminopyridine, 2,4-diaminophenoxyethanol, 1,3-bis-(2,4-diamino-phenoxy)-propane, 2-aminomethyl-3-amino-6-methoxypyridine and 2,6-dihydroxy-3,4-dimethylpyridine.

In this embodiment, it can be preferred to use a hybrid dye of formula (I) containing a group Y derived from an oxidation dye precursor of the secondary intermediate type in combination with at least one other oxidation dye precursor of the primary intermediate type, to use a hybrid dye of formula (I) containing a group Y derived from an oxidation dye precursor of the primary intermediate type in combination with at least one other oxidation dye precursor of the secondary intermediate type to use a hybrid dye of formula (I) containing a group Y derived a derivative of indole or indoline as a melanin precursor in combination with at least one other oxidation dye precursor of the secondary intermediate type.

In a second embodiment, preferred colorants contain at least one substantive dye in addition to a hybrid dye of formula (I).

Substantive dyes suitable for use in accordance with the invention are, for example, nitrophenytlenediamines, nitroaminophenols, azo dyes, anthraquinones and indophenols. Preferred substantive dyes are the compounds known under the International names or commercial names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 1,4-bis-(β-hydroxyethyl)-amino-2-nitrobenzene, 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy4-nitrobenzene. The cationic substantive dyes marked under the name of Arianor® are particularly preferred substantive dyes.

The compositions according to the invention may also contain naturally occurring dyes such as, for example, henna red, henna neutral, camomile blossom, sandalwood, black tea, black alder bark, sage, logwood, madder root, catechu, sedre and alkanet.

The compositions according to the invention of this embodiment contain the substantive dyes in a quantity of preferably 0.01 to 20% by weight, based on the colorant as a whole.

In a third embodiment, colorants which contain at least one derivative of indole or indoline as a melanin precursor in addition to a hybrid dye of formula (I) are particularly preferred.

According to the invention, preferred indoles and indolines are those which contain at least one hydroxy or amino group, preferably as a substituent on the six-membered ring. These groups may carry other substituents, for example in the form of etherification or esterification of the hydroxy group or alkylation of the amino group. Compounds containing two of these groups, particularly two hydroxy groups, of which one or both may be etherified or esterified are particularly preferred.

According to the invention, particularly preferred dye precursors are derivatives of indoline, such as 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 5hydroxyindoline 6-hydroxyindoline, 5-aminoindoline, 6-aminoindoline and 4-aminoindoline.

Most particularly preferred dye precursors are derivatives of 5,6-dihydroxyindoline corresponding to formula (IIIa):

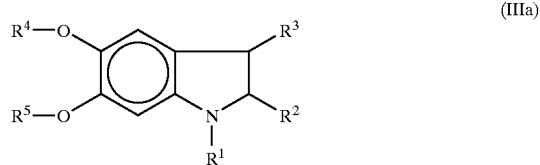

(IIIa)

in which—independently of one another—

$R^1$ is hydrogen, a $C_{1-4}$ alkyl group, a $C_{1-4}$ hydroxyalkyl group or a $C_{3-6}$ cycloalkyl group, $R^2$ is hydrogen or a —COOH group which may even be present as a salt with a physiologically compatible anion, $R^3$ is hydrogen or a $C_{1-4}$ alkyl group, $R^4$ is hydrogen, a $C_{1-4}$ alkyl group or a group —CO—$R^6$ where $R^6$ is a $C_{1-4}$ alkyl group or an optionally substituted phenyl group, $R^5$ stands for one of the groups mentioned for $R^4$, or a physiologically compatible salt of these compounds with an organic or inorganic acid.

According to the invention, preferred representatives are 5,6-dihydroxyindoline, N-methyl-5,6-dihydroxyindoline, N-ethyl-5,6-dihydroxy-indoline, N-propyl-5,6-dihydroxyindoline, N-butyl-5,6-dihydroxyindoline. The parent compound, 5,6-dihydroxyindoline, is most particularly preferred.

According to the invention, preferred indoles are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole, 5,6-dihydroxyindole-2-carboxylic acid, 5-hydroxyindole, 6-hydroxyindole, 5-aminoindole, 6-aminoindole and 4-aminoindole.

Particular preference is attributed to derivatives of 5,6-dihydroxyindole corresponding to formula (IIIb):

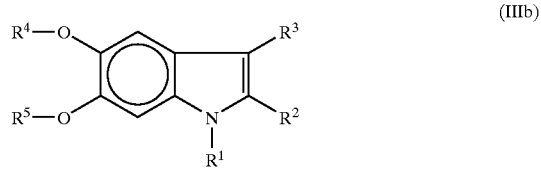

(IIIb)

in which—independently of one another—
R$^1$ is hydrogen, a C$_{1-4}$ alkyl group, a C$_{1-4}$ hydroxyalkyl group or a C$_{3-6}$ cycloalkyl group,
R$^2$ is hydrogen or a —COOH group which may even be present as a salt with a physiologically compatible anion,
R$^3$ is hydrogen, a C$_{1-4}$ alkyl group or a group —CH$_2$—NR$^7$R$^8$ where R$^7$ and R$^8$ independently of one another represent hydrogen or a C$_{1-4}$ alkyl group,
R$^4$ is hydrogen, a C$_{1-4}$ alkyl group or a group —CO—R$^6$ where R$^6$ is a C$_{1-4}$ alkyl group or an optionally substituted phenyl group and
R$_5$ stands for one of the groups mentioned for R$^4$, or a physiologically compatible salt of these compounds with an organic or inorganic acid.

According to the invention, preferred representatives are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole. The parent compound, 5,6-dihydroxyindole, is most particularly preferred.

The present invention does of course also encompass compositions containing more than one indoline or indole derivative or mixtures of indoline and indole derivatives.

The indole or indoline derivatives are present in the compositions according to the invention in quantities of normally 0.05 to 10% by weight and preferably 0.2 to 5% by weight.

In this embodiment, it may be preferred
to use a hybrid dye of formula (I) containing a group Y derived from an oxidation dye precursor of the secondary intermediate type in combination with at least one derivative of indole or indoline as a precursor of melanin,
to use a hybrid dye of formula (I) containing a group Y derived from an oxidation dye precursor of the primary intermediate type in combination with at least one derivative of indole or indoline as a precursor of melanin.

In the embodiments mentioned, the oxidation dye precursors, substantive dyes or melanin precursors do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The hybrid dyes, secondary intermediates and primary intermediates containing amino groups and the indoline and indole derivatives may be used both as free bases and in the form of their physiologically compatible salts with inorganic or organic bases, for example hydrochlorides, sulfates and hydrobromides.

With regard to the dyes suitable for use in the hair coloring and tinting formulations according to the invention, reference is also specifically made to Ch. Zviak's work The Science of Hair Care, Chapter 7 (pages 248–250; Substantive Dyes) and Chapter 8, pages 264–267; Oxidation Dye Precursors), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel e.V., Mannheim, Germany.

In a preferred variant of this embodiment, compositions according to the invention containing a hybrid dye of formula (I) in which the group Y derives from a melanin precursor of the indole or indoline type contain no dyes or dye precursors other than the hybrid dyes mentioned.

In another preferred variant, compositions according to the invention containing a hybrid dye of formula (I), in which the group Y derives from a melanin precursor of the indole or indoline type, and/or a melanin precursor additionally contain at least one amino acid or oligopeptide.

Amino acids in the context of the invention are substances which contain at least one amino group and at least one —COOH or —SO$_3$H group.

Preferred amino acids are aminocarboxylic acids, more particularly (α-aminocarboxylic acids and ω-aminocarboxylic acids. Among the α-aminocarboxylic acids, arginine, lysine, ornithine and histidine are particularly preferred.

The amino acids are preferably added to the formulations according to the invention in free form. However, the amino acids may also be used in salt form. Preferred salts are the compounds containing hydrohalic acids, more particularly hydrochlorides and hydrobromides.

Particularly preferred amino acids are lysine and particularly arginine used in particular in free form but also as the hydrochloride.

In addition, the amino acids may also be used in the form of oligopeptides and protein hydrolyzates providing steps are taken to ensure that the necessary quantities of compounds conforming to the definition of amino acids according to the invention are present. Reference is expressly made in this connection to the disclosure of DE-OS 22 15 303.

The present invention does of course also encompass compositions containing two or more amino acids or oligopeptides. Combinations of arginine with another amino acid or an oligopeptide are preferred.

The compositions according to the invention contain the amino acid or oligopeptide in quantities of preferably 0.1 to 10% by weight and more preferably 1 to 4% by weight, based on the composition as a whole.

Hair colorants, more particularly those where the color is developed oxidatively with atmospheric oxygen or other oxidizing agents, such as hydrogen peroxide, are normally adjusted to a mildly acidic or alkaline pH value, i.e. to a pH value in the range from about 5 to 11. To this end, the colorants contain alkalizing agents, normally alkali metal or alkaline earth metal hydroxides, ammonia or organic amines.

In one special embodiment of the present invention, the amino acid or the oligopeptide is used not only to intensify color development, but also at least partly as an alkalizing agent. Accordingly, amino acids and oligopeptides of which 2.5% by weight solutions in water have a pH value of 9 or higher are preferably used in this embodiment. Such amino acids are the preferred compounds arginine and lysine. In this particular embodiment, the other alkalizing agent is preferably selected from the group consisting of monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine and alkali metal and alkaline earth metal hydroxides. Within this group, monoethanolamine, triethanolamine and 2-amino-2-methylpropanol and 2-amino-2-methyl-1,3-propanediol are particularly preferred. ω-Amino acids, such as ω-aminocaproic acid, are also preferably used as alkalizing agents in this embodiment of the invention.

Particularly advantageous properties are exhibited by formulations in which the amino acid or the oligopeptide and the other alkalizing agent are present in a ratio by weight of 1:5 to 5:1. Quantity ratios of 1:2 to 2:1 have proved to be particularly suitable.

To produce the colorants according to the invention, the compulsory and optional constituents mentioned above are incorporated in a suitable water-containing carrier. Such carriers are, for example, cremes, emulsions, gels or even surfactant-containing foaming solutions, for example shampoos, foam aerosols or other preparations suitable for application to the hair. These preparations are adjusted to a pH value of preferably 5 to 11 and, more preferably, 7 to 10 with the above-mentioned alkalizing agents or suitable acids such as, in particular, food-grade acids, such as citric acid, tartaric acid, lactic acid and acetic acid.

The colorants according to the invention may also contain any of the known active substances, additives and auxiliaries typical of such preparations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment preparations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the corresponding products commercially available as Dehyquart®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

According to the invention, the use of anionic surfactants in combination with zwitterionic surfactants can be particularly preferred.

According to the invention, compositions additionally containing a cationic polymer are also preferred.

Among the cationic polymers, the permanently cationic polymers are preferred. According to the invention, "permanently cationic polymers" are polymers which contain a cationic group irrespective of the pH of the composition. These are generally polymers which contain a quaternary nitrogen atom, for example in the form of an ammonium group. Preferred cationic polymers are, for example, the quaternized cellulose derivatives commercially available under the names of Celquat® and Polymer JR®. The compounds Celquat® H 100, Celquat® L 200 and Polymer JR® 400 are preferred quaternized cellulose derivatives, polysiloxanes containing quaternary groups such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80), cationic guar derivatives such as, in particular, the products marketed under the names of Cosmedia® Guar and Jaguar®), polymeric dimethyl diallyl ammonium salts and copolymers thereof with esters and amides of acrylic acid and methacrylic acid. The products commercially available under the names of Merquat® 100 (poly(dimethyl diallylammonium chloride)) and Merquat® 550 (dimethyl diallylammonium chloride/acrylamide copolymer) are examples of such cationic polymers, copolymers of vinyl pyrrolidone with quaternized derivatives of dialkylaminoacrylate and methacrylate such as, for example, vinyl pyrrolidone/dimethylamino methacrylate copolymers quaternized with diethyl sulfate. Such compounds are commercially available under the name of Gafquat® 734 and Gafquat® 755, The vinyl pyrrolidones/vinyl imidazolinium methochloride copolymers commercially available under the name of Luviquat® FC 370, FC 550, FC 905 and HM 552, quaternized polyvinyl alcohol;

and the polymers containing quaternary nitrogen atoms in the main polymer chain known under the names of Polyquaternium 2, Polyquaternium 17, Polyquaternium 18 and Polyquaternium 27.

Other suitable cationic polymers are the polymers known by the names of Polyquaternium-24 (commercial product: Quatrisoft® LM 200 for example), Polyquaternium-32, Polyquaternium-35 and Polyquaternium-37 (commercial products: Salcare® SC 92 and Salcare® SC 95). Also suitable for use in accordance with the invention are the vinyl pyrrolidone copolymers known by the commercial names of Copolymer 845 (manufacturer: ISP), Gaffix® VC 713 (manufacturer: ISP), Gafquat® ASCP 1011, Gafquat® HS 110, Luviquat® 8155 and Luviquat® MS 370.

According to the invention preferred cationic polymers are quaternized cellulose derivatives, polymeric dimethyl diallyl ammonium salts, Polyquaternium-27 and copolymers thereof and polymers of the Polyquaternium-2 type. Cationic cellulose derivatives, more particularly the commercial product Polymer® JR 400, and polymers of the Polyquaternium-2 type, more particularly the commercial product Mirapol® A-15, are most particularly preferred cationic polymers.

The cationic polymers are present in the compositions according to the invention in quantities of preferably 0.05 to 5% by weight, based on the composition as a whole.

In many cases, amphopolymers may also be used as an alternative to the cationic polymers. Amphopolymers are amphoteric polymers, i.e. polymers which contain both free amino groups and free —COOH or —$SO_3H$ groups in the molecule and which are capable of forming inner salts, zwitterionic polymers which contain quaternary ammonium groups and —$COO^-$or —$SO_3^-$groups in the molecule and polymers which contain —COOH— or $SO_3H$ groups and quaternary ammonium groups. One example of an amphopolymer suitable for use in accordance with the invention is the acrylate resin commercially available as Amphomer® which is a copolymer of tert.butylaminoethyl methacrylate, N-(1,1,3,3-tetramethylbutyl)-acrylamide and two or more monomers from the group consisting of acrylic acid, methacrylic acid and simple esters thereof. Other preferred amphopolymers consist of unsaturated carboxylic acids (for example acrylic and methacrylic acid), cationically derivatized unsaturated carboxylic acids (for example acrylamidopropyl trimethyl ammonium chloride) and optionally other ionic or nonionic monomers of the type disclosed, for example, in DE-OS 39 29 973 and the prior art literature cited therein. According to the invention, terpolymers of acrylic acid, methyl acrylate and methacrylamidopropyl trimonium chloride, which are commercially available under the name of Merquat® 2001 N, and the commercial product Merquat® 280 may also be used as amphopolymers.

The compositions according to the invention also contain at least one nonionic or anionic polymer with thickening properties, preferably optionally crosslinked polyacrylic acids, cellulose derivatives, for example methyl cellulose, hydroxyalkyl cellulose and carboxymethyl cellulose, and xanthan gum.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, gum arabic, karaya gum, locust bean gum, linseed gums, dextrans, starch fractions and derivatives, such as amylose, amylopectin and dextrins, clays such as, for example, bentonite or fully synthetic hydrocolloids such as, for example, polyvinyl alcohol, structurants, such as glucose, maleic acid and lactic acid, hair-conditioning compounds, such as phospholipids, for example soybean lecithin, egg lecithin and kephalins, and also silicone oils, protein hydrolyzates, more particularly elastin, collagen, keratin, milk protein, soybean protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol, diethylene glycol, ethoxybutanol and butoxyethanol and also benzyl alcohol, antidandruff agents, such as Piroctone Olamine and Zinc Omadine, other substances for adjusting the pH value, such as for example α- and β-hydroxycarboxylic acids, active principles, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlizers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

Information on the other constituents of the colorants according to the invention can be found in the reference books known to the expert, for example Umbach, Kosmetik, 2nd Edition, Georg Thieme Verlag, Stuttgart/New York, 1995 and Kh. Schrader, Grundlagen und Rezepturen der Kosmetika, 2nd Edition, Huthig Buch Verlag, Heidelberg, 1989.

Known processes may be used to develop the color on the keratin fiber.

Hair colorants containing one or more hybrid dyes in which the groups X and Y are derived from substantive dyes and which contain no other dye precursors may be applied to the hair in the same way as conventional tinting preparations. These preparations are normally washed off after a certain contact time and the hair is optionally subjected to an aftertreatment. However, where it is used in a hair mascara, the colorant may also be applied to the hair, but especially to individual hair tresses, with an application aid and left on the hair.

In another embodiment, the color is developed with atmospheric oxygen as sole oxidizing agent. This embodiment is particularly preferred when the group Y of the hybrid dye is derived from a melanin precursor or "air-oxidizable" primary and secondary intermediates or when the compositions contains melanin precursors and/or "air-oxidizable" oxidation dye precursors of the primary or secondary intermediate type. In the context of the invention, air-oxidizable compounds are compounds or dye precursors where oxidative development of the final color can be carried out solely with atmospheric oxygen, i.e. without using typical chemical oxidizing agents. Triaminobenzene derivatives are examples of such air-oxidizable compounds.

The use of a chemical oxidizing agent can be preferred in many cases, particularly in cases where the group Y of the hybrid dye derives from a melanin precursor or primary or secondary intermediates or where the composition contains melanin precursors and/or dye precursors of the primary or secondary intermediate type. The same also applies when the hair is not only to be colored, but also lightened. In such cases, a particularly suitable oxidizing agent is hydrogen peroxide or an addition product thereof onto urea, melamine or sodium borate.

The preparation of the oxidizing agent is preferably mixed with the preparation containing the dye precursors immediately before colouring of the hair. The ready-to-use hair colouring preparation formed should preferably have a pH value of 5 to 11. In a particularly preferred embodiment, the hair colorant is used in a mildly alkaline medium. The application temperatures may be in the range from 15 to 40° C. and are preferably at the temperature of the scalp. After a contact time of ca. 5 to 45 and more particularly 15 to 30 minutes, the hair colorant is rinsed out from the hair to be colored. There is no need to wash the hair with a shampoo if a high-surfactant carrier, for example a colouring shampoo, has been used.

The preparation containing the dye precursors may be applied to the hair without premixing with the oxidation component, particularly where the hair is difficult to dye. After a contact time of 20 to 30 minutes, the oxidation component is applied, optionally after rinsing. After a further contact time of 10 to 20 minutes, the hair is rinsed and if desired washed with shampoo. In a first variant of this embodiment where the previous application of the dye precursors is intended to produce better penetration into the hair, the corresponding preparation is adjusted to a pH of about 4 to 7. In a second variant, oxidation with air is carried out first, the preparation applied preferably having a pH of 7 to 10. In the subsequent accelerated post-oxidation step, it may be preferred to use acidified peroxydisulfate solutions as the oxidizing agent. In one particular embodiment of this process, the final color is developed by repeated application of the preparation followed each time by oxidation with air. The preparation is preferably applied at intervals of about one day to about two weeks. Special shades can be obtained very selectively in this way.

Irrespective of which of the above-mentioned processes is used to apply the composition according to the invention, color development can be supported and increased by adding certain metal ions to the composition. Such metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. In principle, the metal ions may be used in the form of a physiologically compatible salt. Preferred salts are the acetates, sulfates, halides, lactates and tartrates. The use of these metal salts enables color development to be accelerated and shades to be influenced as required.

According to the invention, oxidation may also be carried out with enzymes. The enzymes (enzyme class 1: oxidoreductases) are capable of transferring electrons from suitable primary intermediates (reducing agents) to atmospheric oxygen. Preferred enzymes are oxidases, such tyrosinase and laccase, although glucoseoxidase, ascorbate-oxidase uricase or pyruvate oxidase may also be used. In addition, the enzymes may be used to strengthen the effect of small quantities of oxidizing agents present. One example of such an enzymatic process is the procedure whereby the effect of small quantities (for example 1% and less, based on the composition as a whole) of hydrogen peroxide is strengthened by peroxidases.

The present invention also relates to the use of a hybrid dye corresponding to formula (I) or a mixture of these hybrid dyes for coloring keratin fibers, more particularly human hair.

It has also been found that the hybrid dyes according to the invention are also eminently suitable for coloring human skin, more particularly for "tanning" human skin. Accordingly, the present invention also relates to the use of a hybrid dye of formula (I) or a mixture of these hybrid dyes for coloring human skin.

The following Examples are intended to illustrate the invention.

EXAMPLES

1. Syntheses 1.1. 1-((3-((4-aminophenyl)-amino)-propyl)-amino)-anthracene-9,10-dione (hybrid dye A)

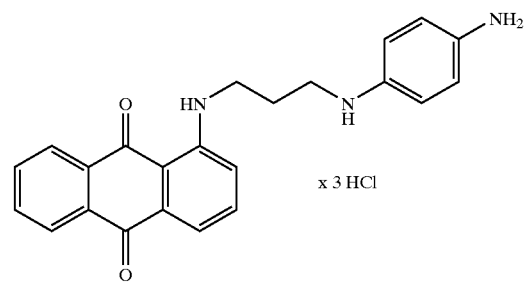

X derived from a substantive dye (1-aminoanthracene-9,10-dione)

Y derived from an oxidation dye precursor of the primary intermediate type (p-phenylenediamine)

S alkylene group (—$CH_2$—$CH_2$—$CH_2$—)

1st Stage

A mixture of 3.73 g (0.015 mole) of 1-chloroanthraquinone, 3.00 g (0.015 mole) of N-(p-nitrophenyl)-propylenediamine, 1.54 g (0.011 mole) of potassium carbonate and 0.13 g of Cu powder in 40 ml of DMSO was reacted with stirring under nitrogen for 1.5 h at 120–130° C. After cooling, the residue was filtered off and recrystallized from acetone/water. 1-((3-((4-aminophenyl)-amino)-propyl)-amino)-anthracene-9, 10-dione (melting point: 183–185° C.), a red powder, was obtained in a yield of 1.4 g.

2nd Stage

A solution of 1.00 g (2.4 mmoles) of 1-((3-((4-aminophenyl)-amino)-propyl)amino)-anthracene-9,10-dione in 340 ml of ethanol was hydrogenated at 25° C. (1013 mbar) in the presence of 0.2 g Pd (5%) on carbon. After the uptake of hydrogen has stopped, the solution was acidified with dilute hydrochloric acid, filtered off from the catalyst and concentrated to dryness. A red solid with a melting point above 170° C. (decomp.) was obtained.

1.2. 1-Amino4-((3-(4aminophenyl)-amino)-propyl)-amino)-anthra-cene-9,10-dione-2-sulfonic acid (hybrid dye B)

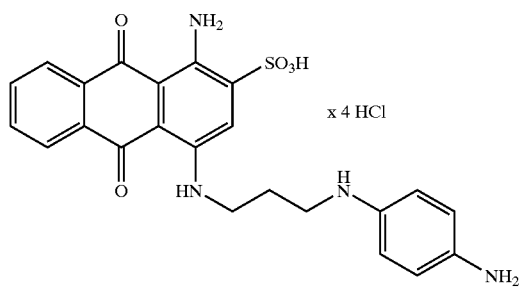

X derived from a substantive dye (1,4-diaminoanthracene-9,10-dione-2-sulfonic acid)

Y derived from an oxidation dye precursor of the primary intermediate type (p-phenylenediamine)

S alkylene group (—CH$_2$—CH$_2$—CH$_2$—)

1st Stage

A mixture of 100.0 g (0.25 mole) of the Na salt of 1-amino-4-bromnoanthraquinone-2-sulfonic acid, 48.3 g (0.25 mole) of N-(p-nitrophenyl)-propylenediamine, 51.8 g (0.37 mole) of potassium carbonate and 0.7 g of Cu powder in 600ml of water were reacted with stirring under nitrogen for 3 h at boiling heat. After cooling, the residue was filtered off and first recrystallized from ethanol/water. The solid thus obtained was dissolved in 1.5 liters of water and adjusted to pH 3.6 with dilute hydrochloric acid. The intermediate product 1-amino-4-((3-((4-nitrophenyl)-amino)-propyl)-amino)-anthracene-9,10-dione-2-sulfonic acid in the form of the free sulfonic acid precipitated as a blue solid (melting point: 215° C.).

2nd Stage

A solution of 15.0 g (0.03 mole) of 1-amino-4-((3-((4-nitrophenyl)-amino)-propyl)-amino)-anthracene-9,10-dione-2-sulfonic acid in 900 ml of ethanol was hydrogenated at 25° C. (1013 mbar) in the presence of 1.0 g Pd (5%) on carbon. After the uptake of hydrogen has stopped, the solution was acidified with dilute hydrochloric acid, filtered off from the catalyst and concentrated to dryness. The product was obtained in the form of a blue-black solid with a melting point above 250° C (decomp.).

1.3. 4-((2-((4-amino-2-nitrophenyl)-amino)-ethyl)-amino)-phenol hybrid dye C)

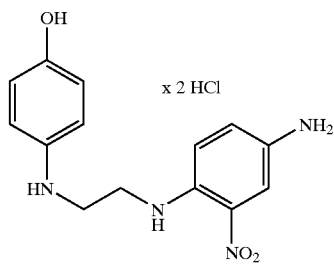

X derived from a substantive dye (4-amino-2-nitroaniline)

Y derived from an oxidation dye precursor of the primary intermediate type (p-aminophenol)

S alkylene group (—CH$_2$—CH$_2$—)

10.0 g (0.04 mole) of p-(β-aminoethylamino)-phenol sulfate (prepared in accordance with U.S. Pat. No. 2,618,657), 8.42 g (42.5 mmoles) of 4-fluoro-3-nitroacetanilide and 6.05 g of sodium hydrogen carbonate were reacted in 40 ml of DMSO with stirring under nitrogen for 3.5 h at a temperature of 65° C. The reaction mixture was then poured onto ice and the deposit was isolated. It was then refluxed for 1 h in 80 ml of dilute hydrochloric acid. The solution was poured onto ice and the deposit 4-((2-((4-amino-2-nitrophenyl)-amino)-ethyl)-amino)-phenol was isolated as a green-brown solid (melting point: 256° C.).

1.4. 4-((2-(2,4-dinitrophenyl)-amino)-ethylamino)-phenol sulfate (hybrid dye D)

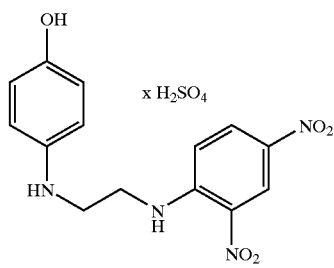

X derived from a substantive dye (2,4-dinitroaniline)

Y derived from an oxidation dye precursor of the primary intermediate type (p-aminophenol)

S alkylene group (—CH$_2$—CH$_2$—)

1st Stage 12.0 g (0.048 mole) of p-(β-aminoethylamino)-phenol sulfate (U.S. Pat. No. 2,618,657), 8.9 g (47.8 mmoles) of 2,4-dinitrofluorobenzene and 6.05 g of potassium carbonate (0.057 mole) were reacted with stirring under nitrogen in 150 ml of ethanol for 2.5 h at boiling heat. The solution was then cooled and filtered off from the salts. The filtrate was adjusted to pH 2 with dilute sulfuric acid, the deposit was isolated and recrystallized from ethanol/water. The product was obtained in the form of brown crystals with a melting point of 238° C. (decomp.).

1.5 (2-((2-amino-4-nitrophenyl)-amino)-ethyl)-naphthylamine (hybrid dye E)

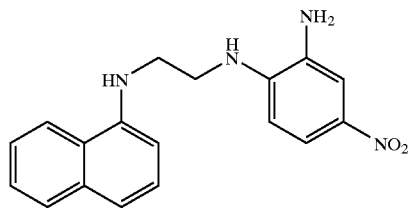

X derived from a substantive dye (2-amino-4-nitroaniline)
Y derived from an oxidation dye precursor of the secondary intermediate type (1-naphthylamine)
S alkylene group (—$CH_2$—$CH_2$—).

1st Stage 10.0 g (38.6 mmoles) of N-(1-naphthyl)-ethylenediamine dihydrochloride were dissolved in a little water and neutralized with dilute sodium hydroxide solution. After the addition of 120 ml of ethanol and 6.4 g of potassium carbonate (46.3 mmoles), 7.2 g (38.7 mmoles) of 2,4-dinitrofluorobenzene were added dropwise. After refluxing for 1 hour, the whole was cooled to room temperature and the deposit was filtered off under suction and washed with water/ethanol. The intermediate product (2-(2,4-dinitrophenyl)-amino)-ethyl)-naphthylamine was obtained in the form of red crystals with a melting point of 263° C.

2nd Stage

A warm solution of 2.5 g (10.5 mmoles) of $Na_2S \times 9H_2O$ and 0.67 g of sulfur in 10 ml of ethanol was added to a solution of 3.7 g (10.5 mmoles) of (2-(2,4-dinitrophenyl)-amino)-ethyl)-naphthylamine and 0.8 g of NaOH in 100 ml of ethanol/67 ml of water. After refluxing for 3 hours, the solution was hot-filtered. The deposit precipitating from the filtrate on cooling was isolated and washed with water/ethanol. The product was obtained in the form of red crystals melting at 149° C.

1.6 (4-amino-2-nitrophenyl)-((3,5-dimethoxyphenyl)-methyl)-amine (hybrid dye F)

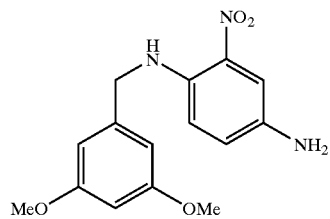

X derived from a substantive dye (4-amino-2-nitroaniline)
Y derived from an oxidation dye precursor of the secondary intermediate type (3,5-dimethoxybenzene)
S alkylene group (—$CH_2$—).

1st Stage

A mixture of 8.0 g (47.8 mmoles) of 3,5-dimethoxybenzylamine, 7.47 g of 4-fluoro-3-nitroaniline (47.8 mmoles) and 7.93 g of potassium carbonate (57.4 mmoles) was refluxed under nitrogen with stirring for 1 h. A deposit precipitated on cooling and was recrystallized from DMF. The product was obtained in the form of dark violet crystals with a melting point of 128° C.

1.7. 2-(5,6-dimethoxyindoliyl)-5-nitrophenylamine/4-(5,6-dimethoxyindoliyl)-3-nitrophenylamine (hybrid dye G)

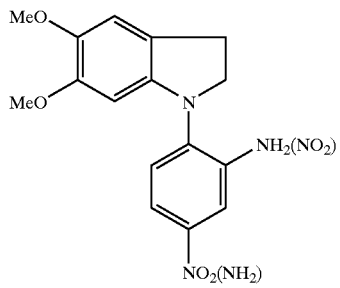

X derived from a substantive dye (3-nitroaniline)
Y derived from a melanin precursor (5,6-dimethoxyindoline)
S direct bond 1st Stage 10.38 g (55.8 mmoles) of 1-fluoro-2,4-nitrobenzene were added with stirring under nitrogen at room temperature to a mixture of 10.0 g (55.8 mmoles) of 5,6-dimethoxyindoline and 11.57 g (83.7 mmoles) of potassium carbonate. After stirring for 3 h, the deposit was isolated and washed with water. The intermediate product 1-(2,4-dinitrophenyl)-5,6-dimethoxy-indoline was obtained as a brown solid with a melting point of 219° C.

2nd Stage

A warm solution of 5.0 g (21 mmoles) of $Na_2S \times 9H_2O$ and 1.34 g of sulfur in 10 ml of ethanol was added to a solution of 7.2 g (20.9 mmoles) of 1-(2,4-dinitrophenyl)-5,6dimethoxyindoline and 0.8 g of NaOH in 200 ml of ethanol/134 ml of water. After refluxing for 3 h, the solution was hot-filtered. Half the filtrate was concentrated and adjusted to pH 7 with concentrated hydrochloric acid. The deposit precipitating on cooling was isolated and washed with water/ethanol. The product was obtained as an isomer mixture (reduction preferably at the ortho as opposed to the para position in a ratio of ca. 4:1, as determined by NMR spectroscopy) in the form of brown crystals with a melting range of about 115 to 130° C.

2. Coloring

A cream base with the following composition was first prepared [all quantities in g unless otherwise indicated]:

| | |
|---|---|
| tallow fatty alcohol | 17.0 |
| Lorol ® techn.[1] | 4.0 |
| Texapon ® N 28[2] | 40.0 |
| Dehyton ® K[3] | 25.0 |
| Eumulgin ® B2[4] | 1.5 |
| distilled water | 12.5 |

[1]$C_{12-18}$ fatty alcohol (HENKEL)
[2]sodium lauryl ether sulfate (ca. 28% active substance; CTFA name: Sodium Laureth Sulfate) (HENKEL)
[3]fatty acid amide derivative of betaine structure with the formula R—$CONH(CH_2)_3N^+(CH_3)_2COO^-$ (ca. 30% active substance; CTFA name: Cocoamidopropyl Betaine) (HENKEL)
[4]cetylstearyl alcohol containing ca. 20 moles EO (CTFA name: Ceteareth-20) (HENKEL)

The following hair coloring cream emulsion was then prepared on the basis of this cream:

| | |
|---|---|
| cream base | 50.0 |
| primary intermediate | 7.5 mmoles |
| secondary intermediate | 7.5 mmoles |

| | |
|---|---|
| Na$_2$SO$_3$ (inhibitor) | 1.0 |
| (NH$_4$)$_2$SO$_4$ | 1.0 |
| conc. ammonia solution to pH 10 | |
| water to 100 | |

The constituents were mixed together in the above order. After addition of the oxidation dye precursors and the inhibitor, the emulsion was first adjusted to pH 10 with concentrated ammonia solution and then made up to 100 g with water.

The color was oxidatively developed with 3% hydrogen peroxide solution as the oxidizing solution. To this end, 50 g of hydrogen peroxide solution (3%) were added to and mixed with 100 g of the emulsion.

The coloring cream was applied to ca. 5 cm long tresses of standardized, 90% gray but not specially pretreated human hair and left thereon for 30 minutes at 32° C. On completion of the coloring process, the hair was rinsed, washed with a standard shampoo and then dried.

The following compounds were used as further dyes/dye precursors:

oxidation dye precursors of the primary intermediate type:

E1 p-toluylenediamine
E2 4-aminophenol
E3 2,4,5,6-tetraaminopyrimidine oxidation dye precursors of the secondary intermediate type:

K1 2,4-diaminophenoxyethanol
K2 1-naphthol
K3 1,3-bis-(2,4-diaminophenoxy)-propane
K4 5-amino-2-methylphenol
K5 4-chlororesorcinol
K6 resorcinol
K7 2-methyl-5-(2'-hydroxyethyl)-aminophenol
K8 3,4-methylenedioxyphenol
K9 2-chloro-6-methyl-3-aminophenol The results of the coloring tests are set out in the following Table:

| Hybrid Dye | Other Dye Precursor | Color of Hair |
|---|---|---|
| A | K1 | Blue-gray |
| A | K2 | Dark blue |
| B | K1 | Black blue |
| B | K3 | Nordic blue |
| B | K2 | Dark blue |
| C | K2 | Ruby red |
| C | K3 | Dark magenta |
| C | K6 | Flat red |
| C | K4 | Flat red |
| C | K5 | Flat red |
| C | K7 | Gray-ruby |
| C | K8 | Dark ruby |
| C | K9 | Flat red |
| D | K6 | Light yellow |
| D | K4 | Yellow-orange |
| D | K3 | Chamois yellow |
| D | K5 | Pastel yellow |
| E | E1 | Loam-colored |
| F | E1 | Flat red |
| G | E1 | Brown-orange |
| G | E3 | Cream-colored |
| G | E2 | Golden blond |
| G | — | Ivory colored[a] |

[a] In this case, coloring was carried out without hydrogen peroxide.

What is claimed is:

1. A composition for coloring keratin fibers comprising a hybrid dye corresponding to formula (I):

X—S—Y  (I)

wherein X is a group derived from a substantive dye;
wherein Y is a group derived from a precursor of melanin that is a derivative of an indoline; and
wherein S is a direct bond or a spacer group.

2. The composition of claim 1 further comprising at least one primary intermediate oxidation dye precursor or secondary intermediate oxidation dye precursor, or combinations thereof.

3. The composition of claim 1 further comprising a substantive dye.

4. The composition of claim 1 further comprising at least one compound selected from a primary intermediate oxidation dye precursor, a secondary intermediate oxidation dye precursor, a substantive dye, or a precursor of melanin that is a derivative of an indole or a derivative of an indoline; or combinations thereof.

5. The composition of claim 4 further comprising at least one additive selected from a surfactant, a cationic polymer, an amphopolymer, an anionic polymer, or a nonionic polymer; or combinations thereof.

6. The composition of claim 1 further comprising a surfactant.

7. The composition of claim 6 wherein the surfactant comprises an anionic surfactant.

8. The composition of claim 1 further comprising at least one cationic polymer or an amphopolymer, or combinations thereof.

9. The composition of claim 1 further comprising at least one anionic polymer or nonionic polymer, or combinations thereof.

10. The composition of claim 1 wherein X is derived from an azo dye, 3-nitroaniline, 2-amino-4-nitroaniline, 2-nitro-1,4-diaminobenzene, a derivative of 2-nitro-1,4-diaminobenzene, a derivative of 4-nitro-2-aminophenol, a derivative of 2-nitro-4-aminophenol, a derivative of 2-nitroaniline, a derivative of quinoxaline, a derivative of anthraquinone, or a derivative of naphthoquinone.

11. The composition of claim 10 wherein Y is derived from 5,6-dimethoxyindoline.

12. The composition of claim 11 wherein S is a direct bond or an alkylene group having 1 to 8 carbon atoms.

13. A method of coloring keratin fibers comprising applying to keratin fibers a hybrid dye corresponding to formula (I):

X—S—Y—  (I)

wherein X is a group derived from a substantive dye;
wherein Y is a group derived from (i) a primary intermediate oxidation dye precursor, (iii) a secondary intermediate oxidation dye precursor, or (ii) a precursor of melanin that is a derivative of an indoline; and
wherein S is a direct bond or a spacer group.

14. The method of claim 13 wherein Y is derived from 3-aminophenol or a derivative thereof, 2-aminophenol or a derivative thereof, 1,3-diaminobenzene or a derivative thereof, 1,2-diaminobenzene or a derivative thereof, dihydroxybenzene or a derivative thereof, trihydroxybenzene or a derivative thereof, a derivative of pyridine, a derivative of naphthalene, a derivative of morpholine, a derivative of quinoxaline, a derivative of pyrazole, a derivative of methylenedioxybenzene, 1,4-diaminobenzene or a derivative thereof, 1,2-diamino benzene or a derivative thereof, 4-aminophenol or a derivative thereof, 2-aminophenol or a derivative thereof, a heterocyclic hydrazone, a pyrimidine derivative, or an indole or an indoline derivative containing at least one hydroxy or amino group substituent.

15. The method of claim 14 wherein X is derived from an azo dye, 3-nitroaniline, 2-amino-4-nitroaniline, 2-nitro-1,4-diaminobenzene, a derivative of 2-nitro-1,4-diaminobenzene, a derivative of 4-nitro-2-aminophenol, a derivative of 2-nitro-4-aminophenol, a derivative of 2-nitroaniline, a derivative of quinoxaline, a derivative of anthraquinone, or a derivative of naphthoquinone.

16. A method of coloring human skin comprising applying to human skin a hybrid dye corresponding to formula (I):

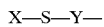  (I)

wherein X is a group derived from a substantive dye;

wherein Y is a group derived from (i) a primary intermediate oxidation dye precursor, (ii) a secondary intermediate oxidation dye precursor, or (iii) a precursor of melanin that is a derivative of an indole or an indoline; and wherein S is a direct bond or a spacer group.

17. A composition for coloring keratin fibers comprising a hybrid dye corresponding to formula (I):

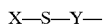  (I)

wherein X is a group derived from a substantive dye;

wherein Y is a group derived from (i) a primary intermediate oxidation dye precursor, or (ii) a secondary intermediate oxidation dye precursor, wherein S is a direct bond or a spacer group; and at least one oxidizing agent.

18. The composition of claim 17 further comprising at least one compound selected from a primary intermediate oxidation dye precursor, a secondary intermediate oxidation dye precursor, a substantive dye, or a precursor of melanin that is a derivative of an indole or a derivative of an indoline; or combinations thereof.

19. The composition of claim 17, wherein the oxidizing agent is selected from hydrogen peroxide or an addition product thereof onto urea, melamine or sodium borate.

20. The composition of claim 17 further comprising at least one additive selected from a surfactant, a cationic polymer, an amphopolymer, an anionic polymer, or a nonionic polymer; or combinations thereof.

21. The composition of claim 17 further comprising a surfactant.

22. The composition of claim 21, wherein the surfactant comprises an anionic surfactant.

23. The composition of claim 17 wherein X is derived from an azo dye, 3-nitroaniline, 2-amino-4-nitroaniline, 2-nitro-1,4-diaminobenzene, a derivative of 2-nitro-1,4-diaminobenzene, a derivative of 4-nitro-2-aminophenol, a derivative of 2-nitro-4-aminophenol, a derivative of 2-nitroaniline, a derivative of quinoxaline, a derivative of anthraquinone, or a derivative of naphthoquinone.

24. The composition of claim 23 wherein Y is derived from 3-aminophenol or a derivative thereof, 2-aminophenol or a derivative thereof, 1,3-diaminobenzene or a derivative thereof, 1,2-diaminobenzene or a derivative thereof, dihydroxybenzene or a derivative thereof, trihydroxybenzene or a derivative thereof, a derivative of pyridine, a derivative of naphthalene, a derivative of morpholine, a derivative of quinoxaline, a derivative of pyrazole, a derivative of methylenedioxybenzene, 1,4-diaminobenzene or a derivative thereof, 1,2-diamino benzene or a derivative thereof, 4-aminophenol or a derivative thereof, 2-aminophenol aminophenol or a derivative thereof, a heterocyclic hydrazone or a pyrimidine derivative.

25. The method of claim 16 wherein Y is derived from 3-aminophenol or a derivative thereof, 2-aminophenol or a derivative thereof, 1,3-diaminobenzene or a derivative thereof, 1,2-diaminobenzene or a derivative thereof, dihydroxybenzene or a derivative thereof, trihydroxybenzene or a derivative thereof, a derivative of pyridine, a derivative of naphthalene, a derivative of morpholine, a derivative of quinoxaline, a derivative of pyrazole, a derivative of methylenedioxybenzene, 1,4-diaminobenzene or a derivative thereof, 1,2-diamino benzene or a derivative thereof, 4-aminophenol or a derivative thereof, 2-aminophenol or a derivative thereof, a heterocyclic hydrazone, a pyrimidine derivative, or an indole or an indoline derivative containing at least one hydroxy or amino group substituent.

26. The method of claim 16 wherein X is derived from an azo dye, 3-nitroaniline, 2-amino-4-nitroaniline, 2-nitro-1,4-diaminobenzene, a derivative of 2-nitro-1,4-diaminobenzene, a derivative of 4-nitro-2-aminophenol, a derivative of 2-nitro-4-aminophenol, a derivative of 2-nitroaniline, a derivative of quinoxaline, a derivative of anthraquinone, or a derivative of naphthoquinone.

27. The hybrid dye 1-((3-((4-aminophenyl)-amino)-propyl)-amino)-anthracene-9,10-dione.

28. The hybrid dye 1-Amino-4-((3-((4-aminophenyl)-amino)-propyl)-amino)-anthracene-9,10-dione-2-sulfonic acid.

29. The hybrid dye 4-((2-((4-amino-2-nitrophenyl)-amino)-ethyl)-amino)-phenol.

30. The hybrid dye 4-((2-((2,4-dinitrophenyl)-amino)-ethylamino)-phenol sulfate.

31. The hybrid dye (2-((2-amino-4-nitrophenyl)-amino)-ethyl)-naphthylamine.

32. The hybrid dye (4-amino-2-nitrophenyl)-((3,5-dimethoxyphenyl)-methyl)-amine.

33. The hybrid dye 2-(5,6-dimethoxyindoliyl)-5-nitrophenylamine/4-(5,6-dimethoxyindolyl)-3-nitrophenylamine.

* * * * *

UNITED STATES PATENT AND TRADEMARK OFFICE
CERTIFICATE OF CORRECTION

PATENT NO. : 6,828,443 B1
DATED : December 7, 2004
INVENTOR(S) : Hollenberg et al.

It is certified that error appears in the above-identified patent and that said Letters Patent is hereby corrected as shown below:

Column 28,
Line 60, delete "X–S–Y–" and insert -- X–S–Y --.
Line 64, delete "(iii)" and insert -- (ii) --.
Line 65, delete "(ii)" and insert -- (iii) --.

Column 29,
Lines 25 and 36, delete "X–S–Y–" and insert -- X–S–Y --.

Column 30,
Lines 19-20, delete the second instance of "aminophenol".
Line 57, delete "dimethoxyindolyl" and insert -- dimethoxyindoliyl --.

Signed and Sealed this

Twenty-third Day of August, 2005

JON W. DUDAS
*Director of the United States Patent and Trademark Office*